(12) United States Patent
Lee (10) Patent No.: US 8,901,514 B2
(45) Date of Patent: Dec. 2, 2014

(54) SAMPLE ANALYSIS SYSTEM WITH SPOTLIGHT ILLUMINATION

(75) Inventor: Chun-Shen Lee, Cupertino, CA (US)

(73) Assignee: Molecular Devices, LLC, Sunnyvale, CA (US)

( * ) Notice: Subject to any disclaimer, the term of this patent is extended or adjusted under 35 U.S.C. 154(b) by 212 days.

(21) Appl. No.: 13/536,106

(22) Filed: Jun. 28, 2012

(65) Prior Publication Data

US 2014/0001375 A1  Jan. 2, 2014

(51) Int. Cl.
*F21V 9/16* (2006.01)
*G01J 1/58* (2006.01)

(52) U.S. Cl.
USPC .................................................. 250/459.1

(58) Field of Classification Search
USPC .................................................. 250/459.1
See application file for complete search history.

(56) References Cited

U.S. PATENT DOCUMENTS

| | | | |
|---|---|---|---|
| 5,355,215 A | 10/1994 | Schroeder et al. | |
| 6,171,866 B1 * | 1/2001 | He et al. | 436/79 |
| 6,930,314 B2 | 8/2005 | Jackson, III et al. | |
| 7,387,891 B2 * | 6/2008 | Boege et al. | 435/288.7 |
| 2002/0100863 A1 * | 8/2002 | Spears | 250/208.1 |
| 2002/0191171 A1 * | 12/2002 | Nishi | 355/67 |
| 2002/0195577 A1 * | 12/2002 | Gann et al. | 250/559.48 |
| 2003/0006364 A1 * | 1/2003 | Katzir et al. | 250/208.1 |
| 2003/0098409 A1 * | 5/2003 | Bond et al. | 250/223 R |
| 2003/0184856 A1 * | 10/2003 | Otaki | 359/383 |
| 2006/0183623 A1 * | 8/2006 | Ikuta et al. | 501/54 |
| 2007/0138419 A1 * | 6/2007 | Bueno et al. | 250/586 |
| 2007/0187580 A1 * | 8/2007 | Kykta et al. | 250/227.15 |
| 2008/0002395 A1 * | 1/2008 | Eisenberg et al. | 362/109 |
| 2010/0007514 A1 * | 1/2010 | Sejkora | 340/825.22 |

OTHER PUBLICATIONS

User Guide: FLIPR Tetra: High throughput Cellular Screening System, Dec. 2011, pp. 1-15; 18-19; 32-39; 273-277.

* cited by examiner

*Primary Examiner* — David Porta
*Assistant Examiner* — Abra Fein
(74) *Attorney, Agent, or Firm* — Bella Fishman (57) ABSTRACT

System, including methods and apparatus, for sample analysis using at least one array of spotlights to illuminate a microplate with excitation light for photoluminescence emission.

14 Claims, 6 Drawing Sheets

SPOT            FLOOD

Fig. 6

SAMPLE ANALYSIS SYSTEM WITH SPOTLIGHT ILLUMINATION

INTRODUCTION

Samples held in wells of a microplate can be analyzed by detecting photoluminescence emission. The samples can contain one or more luminophores that emit light, such as fluorescence or phosphorescence, when illuminated with excitation light of the appropriate wavelength(s). Light-emitting diodes (LEDs) are sources of excitation light that offer low cost, efficiency, and a broad range of available excitation wavelengths.

LEDs producing visible light or ultraviolet radiation may be utilized as light sources for microplate illumination. However, the power level of ultraviolet LEDs can be several orders of magnitude less than for visible LEDs, making ultraviolet systems inaccurate and insensitive. New approaches are needed for better utilizing LEDs in systems with photoluminescence detection.

SUMMARY

The present disclosure provides a system, including methods and apparatus, for sample analysis using at least one array of spotlights to illuminate a microplate with excitation light for photoluminescence emission.

DETAILED DESCRIPTION

The present disclosure provides a system, including methods and apparatus, for sample analysis using at least one array of spotlights to illuminate a microplate with excitation light for photoluminescence emission.

An exemplary system for sample analysis is provided. The system may comprise a support member to hold a microplate in an examination area. The system also may comprise one or more arrays of spotlights that illuminate the examination area with excitation light. The system further may comprise a detector to create one or more images of the microplate by sensing light emitted from the examination area in response to illumination with the excitation light. The system also may comprise a processor programmed to determine a characteristic of samples contained in individual wells of the microplate based on the images. In some embodiments, the spotlights in each array may be arranged in two or more rows and/or may not be spaced uniformly within each row. In some embodiments, the detector may have a nonuniform sensitivity to the emitted light received from different regions of the examination area, and the spotlights may be arranged to illuminate the examination area unevenly to compensate for the nonuniform sensitivity of the detector. In some embodiments, the microplate has a footprint, and each spotlight has a maximum intensity and may illuminate less than about one-fourth of the footprint at half maximal or greater intensity.

An exemplary method of sample analysis is provided. In the method, a microplate may be illuminated in an examination area with excitation light from one or more arrays of spotlights. Wells of the microplate may contain samples that include a luminophore, such as a fluorophore or phosphor. One or more images of the microplate may be created by sensing light emitted from the luminophore in the examination area in response to illumination with the excitation light. A characteristic of the samples may be determined based on the images. In some embodiments, the characteristic may a calcium level and/or the luminophore may be Fura-2.

A sample analysis system with spotlight illumination may provide substantial advantages over similar systems using floodlight illumination. These advantages may include more uniform illumination; finer control over the illumination pattern produced, to permit compensation for nonuniform detector sensitivity through corresponding changes in the illumination pattern; more efficient use of light because a greater percentage of light can be aimed at the examination area; or any combination thereof, among others.

Further aspects of the present disclosure are presented in the following sections: (I) exemplary sample analysis system with photoluminescence detection, (II) samples and methods of sample analysis, and (III) examples.

I. EXEMPLARY SAMPLE ANALYSIS SYSTEM WITH PHOTOLUMINESCENCE DETECTION

This section describes an exemplary sample analysis system 20 for collecting photoluminescence data from samples 22 held by a microplate 24; see FIGS. 1-5.

Figure 1:
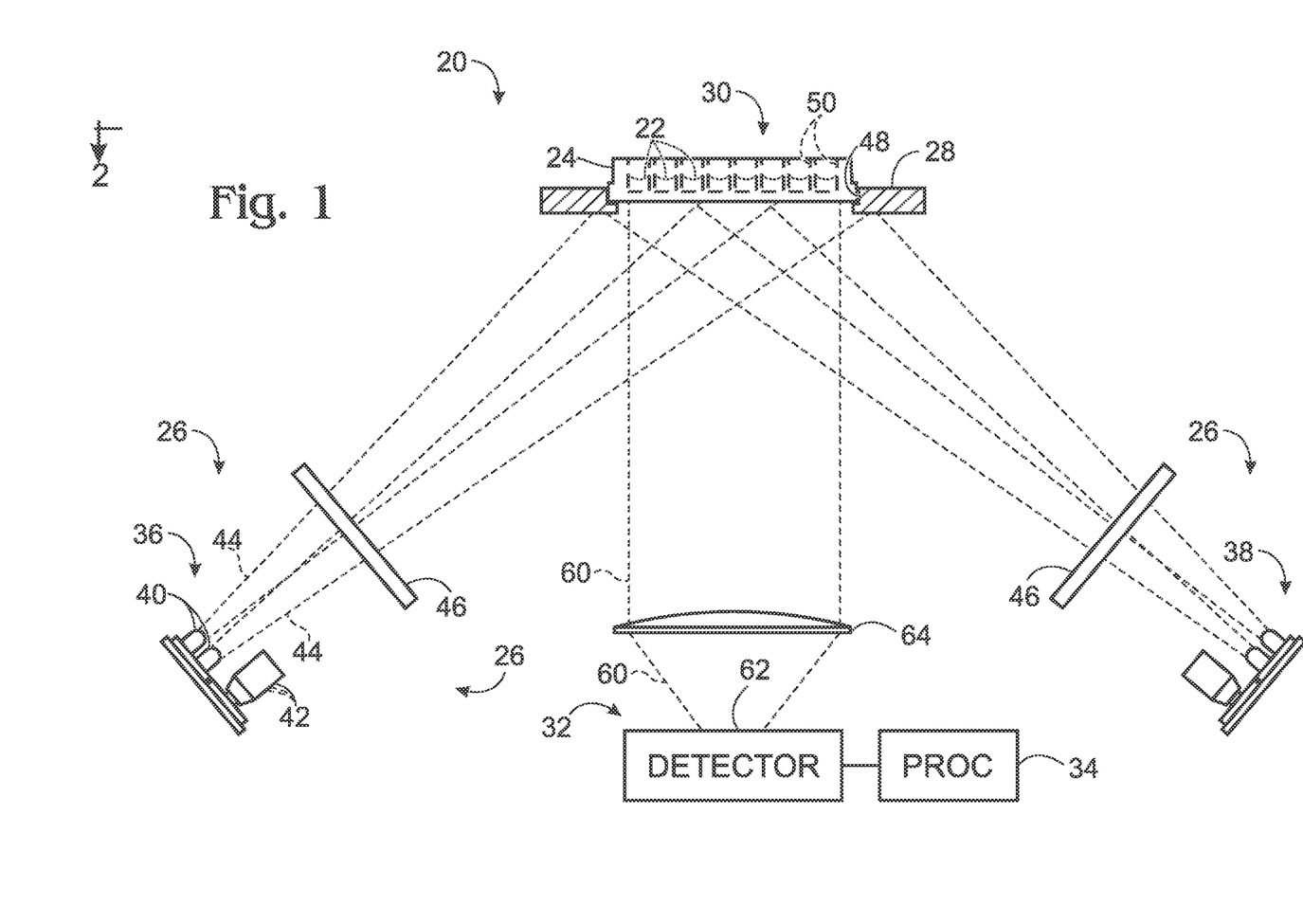
FIG. 1 is a side view of selected aspects of an exemplary sample analysis system for detecting photoluminescence emission from samples held in wells of a microplate and illuminated with excitation light from one or more arrays of spotlights, in accordance with aspects of the present disclosure.

FIG. 1 shows a somewhat schematic side view of system 20, with only selected components visible. The system may include an illumination portion 26 to illuminate the microplate with excitation light, a stage or support portion 28 to hold microplate 24 in an examination area 30, a detection portion 32 that creates images of the microplate by detecting light emitted from the examination area, and a processor 34 to manipulate data from the images. (The term "light," when used to describe a type of electromagnetic radiation, may include any optical radiation, namely, ultraviolet radiation, visible light, and infrared radiation.)

Illumination portion 26 may serve as a source of excitation light to produce photoluminescence emission from sample 22. The illumination portion may be composed of one or more light assemblies 36, 38 arranged in a spaced relation to each other below (or above examination area 30). For example, here, each light assembly is arranged below the microplate and on generally opposite lateral sides of microplate 24. The light assembly may be arranged obliquely to horizontal and vertical axes/planes, such as mounted at an angle of about 30 to 60 degrees with respect to horizontal and vertical, as determined by a plane defined by the light assembly and/or light beams therefrom. An oblique arrangement may reduce the amount of excitation light incident on the detector.

Each light assembly may provide one or more arrays of lights (i.e., light sources). For example, here, each light assembly is composed of an array of spotlights 40 and an array of floodlights 42. Exemplary narrow beams 44 emitted from the spotlights are indicated with dashed lines extending from the spotlights to examination area 30, and particularly to microplate 24 held therein.

Illumination portion 26 also may include optics, namely, one or more optical elements that transmit, direct, and/or modify light emitted from the spotlights and/or floodlights. Exemplary optical elements may include (1) transmissive or conductive elements (such as fiber optics or light guides), (2) reflective elements (such as mirrors), (3) refractive elements (such as lenses), (4) subtractive elements (such as filters), and/or (5) diffractive elements (such as gratings), among others. For example, in the present illustration, a wavelength-dependent filter 46 (e.g., a cutoff filter, a bandpass filter, or the like) is operatively disposed on the path traveled by light between each light assembly and examination area 30. In other embodiments, a polarizing filter also or alternatively may be included.

Illumination portion 26 may have any suitable position relative to detection portion 32. The illumination portion may be on the same side of microplate 24 as the detection portion (e.g., with both portions below or both portions above the microplate), to provide epi-illumination, or the portions may be arranged on opposing sides of the microplate (e.g., one portion above and the other below the microplate), to provide trans-illumination.

Support portion 28 may be configured to receive and support one or more microplates 24, such as to support the microplate above illumination portion 26 and/or detection portion 32. The support portion may, for example, define an aperture or window 48 to receive microplate 24 and to permit light to travel from illumination portion 26 to the microplate and from the microplate to detection portion 32. The aperture may be a void or may be composed of a material (solid and/or liquid) that is transparent to excitation and emission light.

Microplate 24 may be any sample holder defining a plurality of wells 50 to hold samples 22, generally in fluid isolation from one another. The wells may be arranged in a two-dimensional array. The array may have any suitable number of wells arranged in rows and columns, such as a 4×6 array (a 24-well microplate), an 8×12 array (a 96-well microplate), a 16×24 array (a 384-well microplate), a 32×48 array (a 1536-well microplate), etc. The microplate may meet any of the standards for microplate structure defined by the Society for Biomolecular Sciences and/or the American National Standards Institute. For example, the footprint of the microplate may be rectangular and may have dimensions of about 130 mm by 85 mm. The center-to-center spacing of wells may be about 1.8, 0.9, 0.45, or 0.225 mm, among others. The capacity or volume of each well may be less than about one milliliter, such as less than about 250, 100, 50, 25, or 10 microliters, among others. The microplate may be flat and formed of a polymer, such as polystyrene, and may be transparent, at least at the positions of the wells. The microplate may be used with or without a cover disposed over the wells.

Detection portion 32, interchangeably termed a detector, may be arranged and configured to receive emitted light 60 from microplate 24. Detector 32 may include an image sensor 62 and any associated optics, among others. For example, here, a lens 64 focuses emitted light 60 onto image sensor 62. Other optical elements that may be suitable for the detector include any combination of the optical elements listed above for illumination portion 26, such as a wavelength-dependent filter disposed between the microplate and detector to block excitation light. The image sensor may be any suitable optical sensing device with spatial resolution to allow creation of an image. The image sensor may be sensitive to optical radiation, namely, ultraviolet radiation, visible light, infrared radiation, or a combination thereof. Suitable image sensors for the sample analysis system may include charge-coupled devices (CCDs), complementary metal-oxide semiconductor (CMOS) arrays, charge-injection devices (CDs), photodiode arrays, arrays of photomultiplier tubes (PMTs), pin photodiodes, avalanche photodiodes, photocells, phototubes, and the like. The image sensor may be sensitive to the intensity, wavelength, polarization, and/or coherence of the detected optical radiation, among other properties, as well as spatial and/or temporal variations thereof.

Processor 34 may be in communication with detector 32, such as via a wired or wireless connection, to allow transfer and processing of image data collected by the detector. The processor may utilize image data obtained by detector 32 to determine one or more characteristics of samples held by the microplate. The processor may be described as a computer and may, for example, include a microprocessor, memory for data storage, instructions for data manipulation, one or more IO ports, a user interface, etc. The processor may be a dedicated component of the system or may, for example, be a personal computer with multi-purpose functionality. In some cases, the processor may be configured as a controller that controls, monitors, and/or coordinates operation of other system components, such as the illumination portion and the detector, a display, a printer, or any combination thereof, among others.

Figure 2:
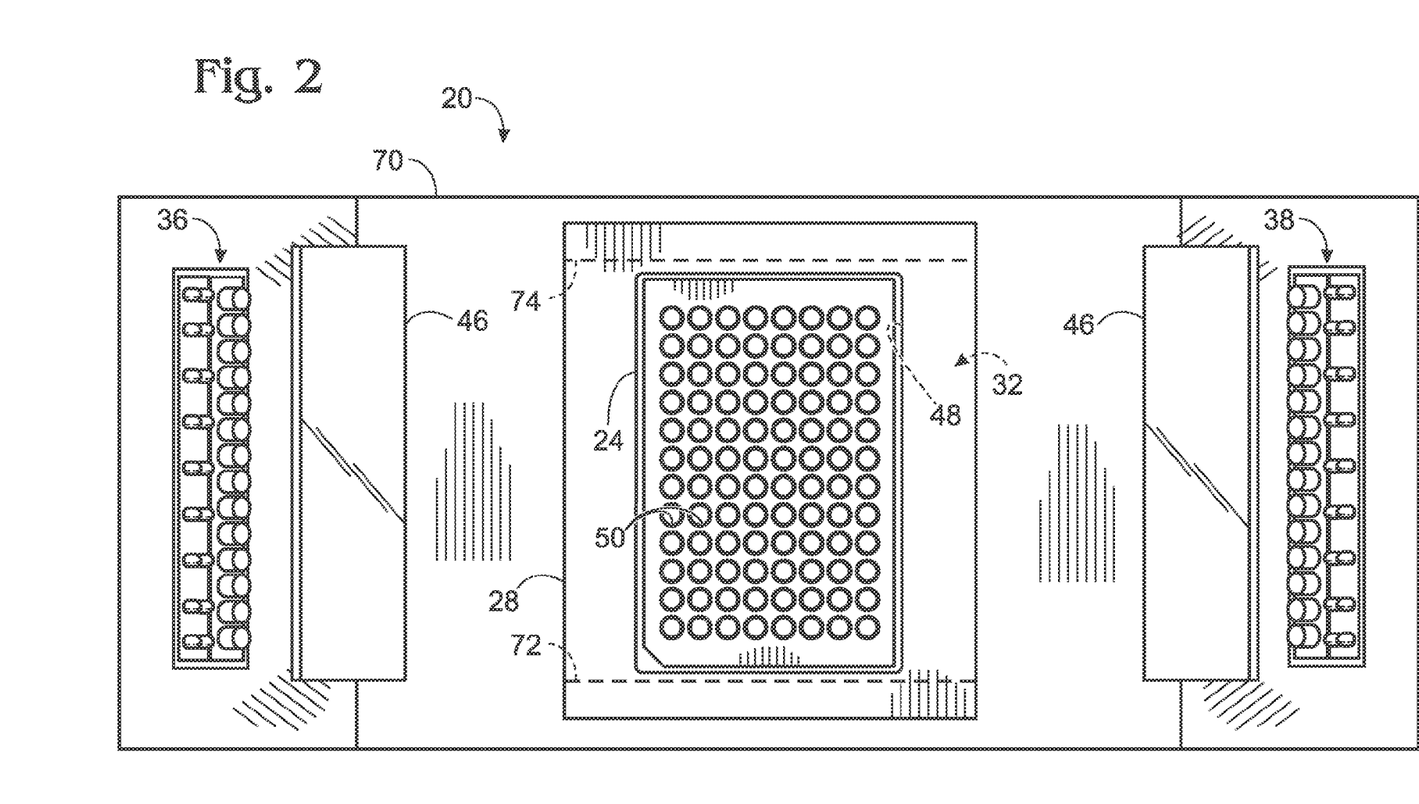
FIG. 2 is a top view of the sample analysis system of FIG. 1, taken in the presence of a housing that holds selected system components in place.

FIG. 2 shows a top view of sample analysis system 20, taken in the presence of a housing or frame 70 that positions (e.g., fixes), supports, and/or protects selected system components. For example, housing 70 may support stage 28 and legs 72, 74 extending from the stage to the housing. The legs may elevate the stage from the base of the housing. Also, light assemblies 36, 38 and filters 46 may be mounted to the housing, such as via brackets. Furthermore, detector 32 may be connected to the housing below stage 28, such as between or under legs 72, 74.

Figure 3:
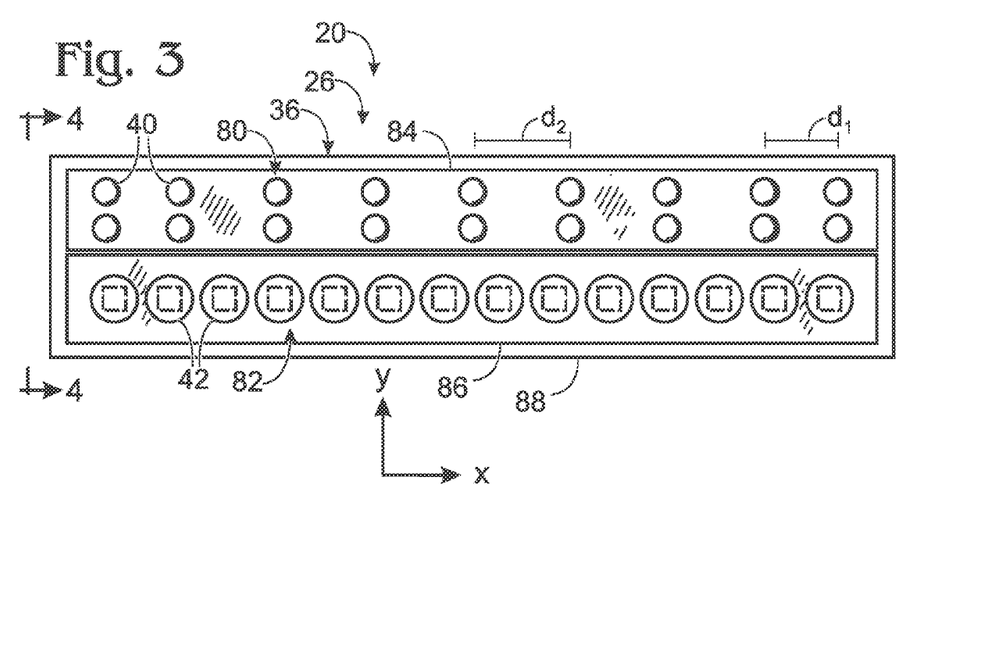
FIG. 3 is a top view of a spotlight array and a floodlight array from the system of FIG. 1, taken orthogonally to each array, with each array being configured to produce light of a different wavelength.

FIG. 3 shows an orthogonal view of light assembly 36 of illumination portion 26 from system 20. The light assembly may include one or more arrays of light sources for irradiating the microplate. For example, the light assembly may be equipped with a spotlight array 80 and a floodlight array 82 composed respectively of spotlights 40 and floodlights 42. The light sources within each array may be configured to emit light of different wavelengths. For example, spotlights 40 may be a source of excitation light of a shorter wavelength or waveband, and floodlights 42 may be a source of excitation light of a longer wavelength or waveband, or vice versa, among others. In some embodiments, the spotlights and/or the floodlights may produce ultraviolet radiation predominantly or substantially exclusively.

The light sources of each array 80, 82 may be attached to a substrate (interchangeably termed a mounting member), namely, substrate 84 or 86, respectively. The substrate may be termed a board (e.g., a printed circuit board). The light sources may be fixed to each substrate such that the relative positions and relative aiming directions of the light sources within each array are fixed relative to one another. Alternatively, in some embodiments, the light sources within an array may be adjustably aimed or positioned with respect to one another after they are placed into the array. The ability to adjust the position or orientation of a given light source independently of other light sources of the array may be beneficial for fine-tuning the illumination pattern generated by the array.

Substrates 84, 86 may be mounted to the same support member 88, which in turn may be mounted to a bracket and/or the housing of the system. Alternatively, arrays 80, 82 may be mounted to the housing independently of one another via their respective substrates 84, 86. In some embodiments, the same substrate may hold more than one array, such as holding spotlights 40 and floodlights 42.

Each array 80, 82 may be a one-dimensional array or at least a two-dimensional array. For example, in the depicted embodiment, array 80 is a two-dimensional array composed of two rows and nine columns of spotlights 40, and array 82 is a one-dimensional array composed of only one row of fourteen floodlights. Each array may have any suitable number of light sources, such as at least 4, 8, or 12, among others.

Array 80 may have any suitable arrangement of row and columns. In the depicted embodiment, the rows are arranged parallel to an x-axis (and to the long axis of the array), which may be a substantially horizontal axis of system 20. The columns of the array may (or may not) be arranged parallel to a local y-axis of the array (i.e., orthogonal to the x-axis), which may be oblique to each of the characteristic axes of system 20 (see FIGS. 1 and 2) when the array is mounted in the system. Alternatively, the columns of the array may be arranged parallel to one of the characteristic axes of system 20, namely, a horizontal axis or a vertical axis. Spotlights 40 may be uniformly or nonuniformly spaced along each axis of the array. For example, in the depicted embodiment (see FIG. 3), the spotlights (and/or columns thereof) are more closely spaced (separated by distance $d_1$) at opposing ends of array 80 relative to a central portion of the array disposed between the opposing ends where the spotlights are rated by distance $d_2$, with $d_2 > d_1$. In other embodiments, the spotlights may be arranged in one row or three or more rows, may be staggered, and/or may be uniformly spaced (see Section III).

Array 82 also may have any suitable arrangement of rows and columns. In the depicted embodiment, floodlights 42 are arranged along a straight line, to form a single row with a uniform spacing of light sources. In other embodiments, the floodlights may be arranged in two or more rows, may be staggered, may have a nonuniform spacing, and/or may be replaced by spotlights, among others.

Figure 4:
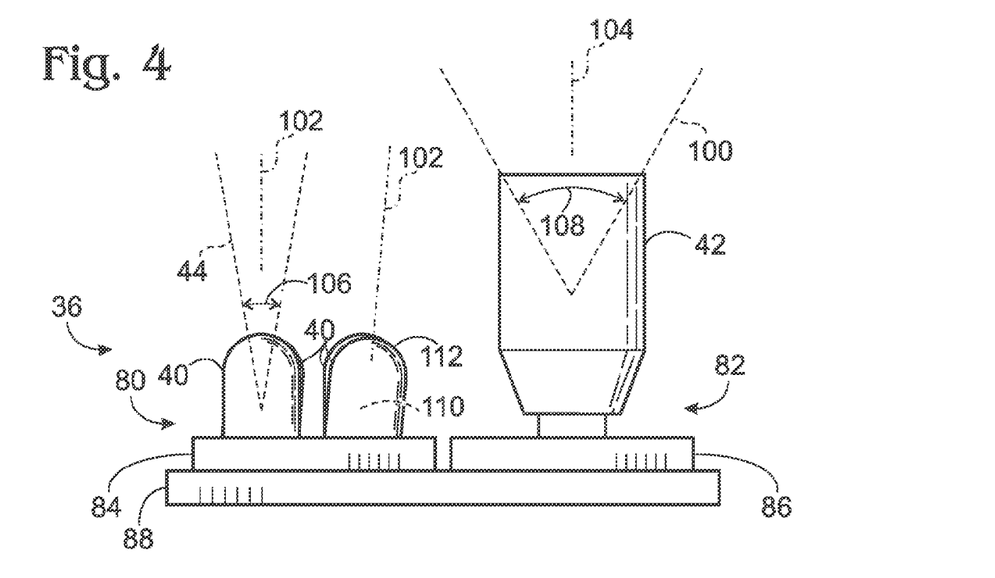
FIG. 4 is an end view of the pair of arrays of FIG. 3, taken generally along line 4-4 of FIG. 3 and illustrating a narrow beam produced by a spotlight and a broad beam produced by a floodlight.

FIG. 4 shows an end view of arrays 80, 82, with beams 44 and 100 being generated by spotlight 40 and floodlight 42, respectively. Spotlights 40 may define optical or central axes 102 that are not parallel to one another. In other words, each spotlight may be aimed appropriately at examination area 30 (see FIG. 1) to achieve a desired coverage and uniformity of illumination for the examination area. In this way, the size and length-to-width ratio of array 80 does not need to match the examination area. For example, the length of array 80 may be greater than the length of the examination area, to spread the spotlights out, which may reduce thermal build-up and overheating. Alternatively, or in addition, the width (and/or length) of the array may be less than the width (and/or length) of the examination area, to make the light assembly more compact. The optical or central axes of the spotlights may be offset by any suitable angle relative to one another, such as about 0-20 degrees, among others. Floodlights 42 also may define optical or central axes 104 that are not parallel to one another, to provide effective illumination of the examination area.

Spotlights 40 and floodlights 42 are distinguished by their angular beam widths 106, 108. Each spotlight produces a narrow beam with a full width at half maximum (FWHM) of less than about 30 degrees (e.g., less than about 25 degrees, among others). In contrast, each floodlight produces a broad beam with a full width at half maximum (FWHM) of at least about 60 degrees. In other words, the spotlight and floodlight may form conical beams having an included angle of less than about 30 degrees or at least about 60 degrees, respectively, measured where the radiation intensity has dropped off to one-half of maximum.

Each light source (spotlight and/or floodlight) may include a light-emitting element and, optionally, at least one optical element 112 associated with the light-emitting element. The light source may be a solid-state device, such as a light-emitting diode (LED) (e.g., a semiconductor LED, an organic LED, or a polymer LED, among others). The term "light-emitting diode" (LED) is intended to encompass the light-emitting element itself and any associated optical element(s) that transmits, directs, modifies, or filters the light emitted by the light-emitting element. For example, an LED may include a diode 110 and a lens or case 112 in which the diode is embedded or enclosed. In the depicted embodiment, for example, spotlight 40 has a diode embedded in a cylindrical lens having a spherical end. In other examples, the light source may be an incandescent light, a fluorescent light, a laser, or the like.

Figure 5:
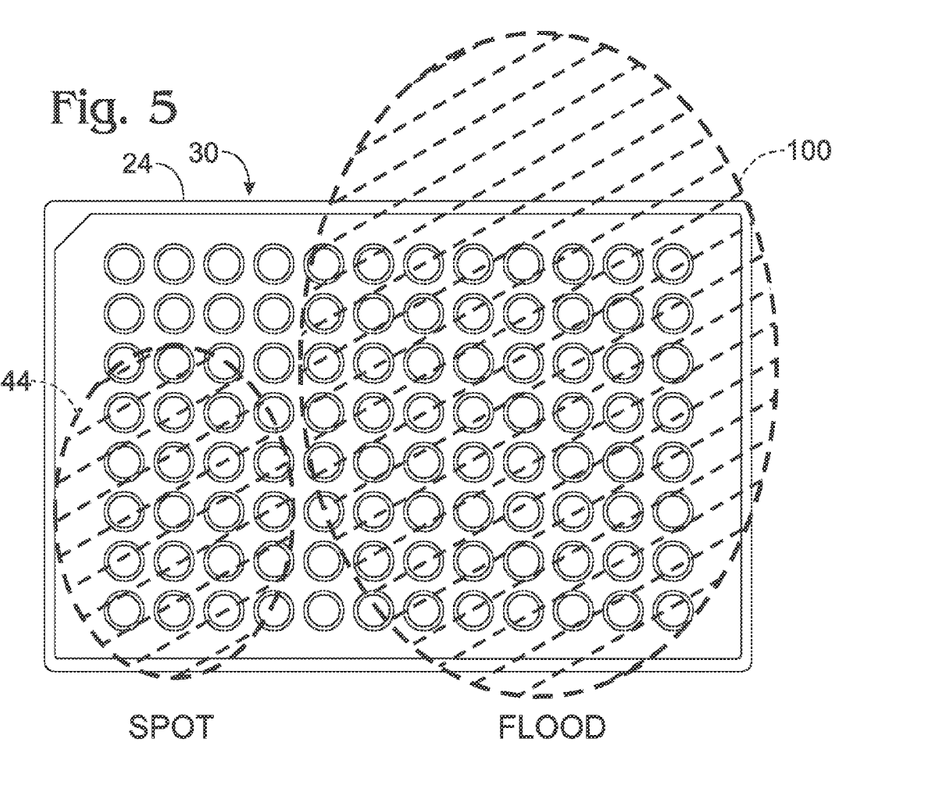
FIG. 5 is a somewhat schematic top view of an exemplary microplate being illuminated with a single spotlight and a single floodlight in the system of FIG. 1, to illustrate the difference in beam width and illumination area produced by the two types of light sources, in accordance with aspects of the present disclosure.

FIG. 5 shows a somewhat schematic top view of microplate 24 being illuminated with a single spotlight (beam 44) and a single floodlight (beam 100) in the system of FIG. 1. Due to its substantially narrower size, spotlight beam 44 may illuminate an area that is significantly smaller than the area illuminated by floodlight beam 100, such as no more than about ⅓, ¼, or ⅕ as large. The use of a narrower beam can improve the efficiency with which the microplate is illuminated, because less light is incident outside the examination area (e.g., compare the two illumination areas of FIG. 5). Therefore, less power and/or fewer lights may be needed. Also, the use of a narrower beam provides finer control over how much light is transmitted to each region of the examination area, which may allow for better uniformity of illumination and/or more precise generation of a desired illumination pattern.

II. SAMPLES AND METHODS OF SAMPLE ANALYSIS

This section describes exemplary samples and methods of analyzing samples using the system disclosed herein.

Any suitable sample may be analyzed. The sample may (or may not) be an aqueous sample from any suitable source, such as a biological sample, an industrial sample, an atmospheric sample, a terrestrial sample, a marine sample, or the like. Exemplary biological samples may be isolated from a patient, soil, water, air, or a culture, among others.

The sample may include any suitable analyte to be tested. Exemplary analytes include an ion or element (e.g., calcium, sodium, potassium, iron, gallium, etc.), a nucleic acid, a protein (e.g., an antibody or enzyme), a peptide, a sugar or polysaccharide, a lipid, a small molecule, an enzyme substrate, an enzyme product, or the like.

The sample may include at least one luminophore capable of photoluminescence when irradiated with suitable excitation light. The luminophore may include an acridine, cyanine, fluorone, oxazin, phenanthridine, or rhodamine dye, among others.

In some examples, the sample may include a calcium-binding dye, such as Fura-2 or Fura-2AM (Fura-2-acetoxymethyl ester). Fura-2 is a calcium indicator, which may be used to measure the level of calcium in a sample, such as the level of intracellular calcium. The level of photoluminescence may be measured in response to excitation at a pair of wavelengths or wavebands (e.g., excitation at about 330-350 nm (about 340 nm) and at about 370-390 nm (about 380 or 385 nm)). For example, spotlights 40 may be used to illuminate samples at about 340 nm and floodlights 42 (or a different set of spotlights) may be used to illuminate samples at about 380-385 nm. The ratio of photoluminescence measured with illumination at the different wavelengths allows determination of calcium levels with greater accuracy.

Any suitable photoluminescence measurements can be obtained. These measurements may include fluorescence intensity, fluorescence polarization, fluorescence lifetime, fluorescence resonance energy transfer, etc., and/or their phosphorescence-based counterparts.

Any suitable sample characteristic(s) may be determined from photoluminescence measurements. The characteristic may be a level (e.g., concentration), activity, location, extent of modulation, etc. The characteristic may be an intensive or extensive property of the sample.

III. EXAMPLES

This section presents selected aspects and embodiments of the present disclosure related to sample analysis systems with spotlight illumination of microplates. These aspects and embodiments are intended for illustration and should not limit the entire scope of the present disclosure.

Example 1

Exemplary Illumination Patterns of a Microplate/Examination Area

Figure 6:
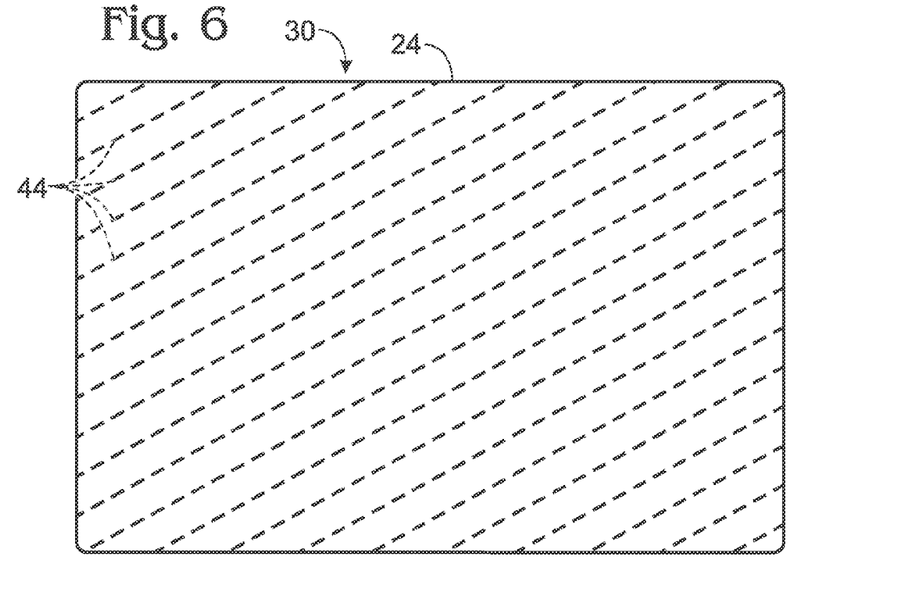
FIG. 6 is a schematic illustration of the examination area and microplate of the system of FIG. 1 being illuminated uniformly by both arrays of spotlights, in accordance with aspects of the present disclosure.
Figure 7:
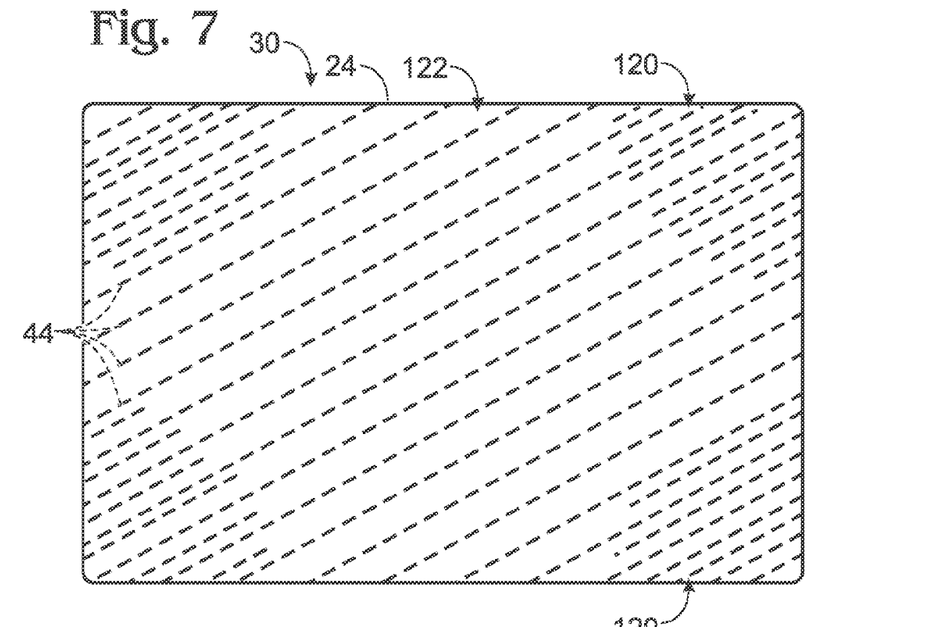
FIG. 7 is a schematic illustration of the examination area and microplate of the system of FIG. 1 being illuminated nonuniformly by both arrays of spotlights, to compensate for a nonuniform sensitivity of an image sensor of detector, in accordance with aspects of the present disclosure.

This example describes exemplary illumination patterns that may be achieved in a sample analysis system with spotlights generating excitation light; see FIGS. 6 and 7.

FIG. 6 shows a schematic illustration of examination area 30 and microplate 24 of system 20 being illuminated uniformly by both arrays of spotlights (see FIGS. 1 and 2). Light from spotlight beams 44 is indicated with dashed lines, with the spacing of the lines inversely related to illumination intensity.

FIG. 7 shows a schematic illustration of examination area 30 and microplate 24 of system 20 being illuminated nonuniformly by both arrays of spotlights (see FIGS. 1 and 2). Corner and/or perimeter regions 120 of the examination area and microplate are illuminated at a higher intensity than a central region 122 of the area/microplate. The nonuniform illumination pattern shown here may be used to compensate for a corresponding nonuniform sensitivity of the image sensor. For example, a CCD imaging system may provide a detection area having higher sensitivity centrally and lower sensitivity near the detection area's perimeter and/or corners ("corner roll-off"). In other words, with uniform illumination, images collected by the imaging system may have dimmer corners and brighter centers. Irradiating corresponding regions of the examination area/microplate with more light can help to compensate for the regions of lower detection sensitivity. Placing a higher density of spotlights at the ends of a spotlight array (e.g., see FIG. 3) may facilitate compensating for perimeter/corner effects of the image sensor.

Example 2

Exemplary Spotlight Arrangements in an Array and/or Light Assembly

This example describes exemplary arrangements of spotlights within one or more arrays; see FIGS. 8-11.

Figure 8:
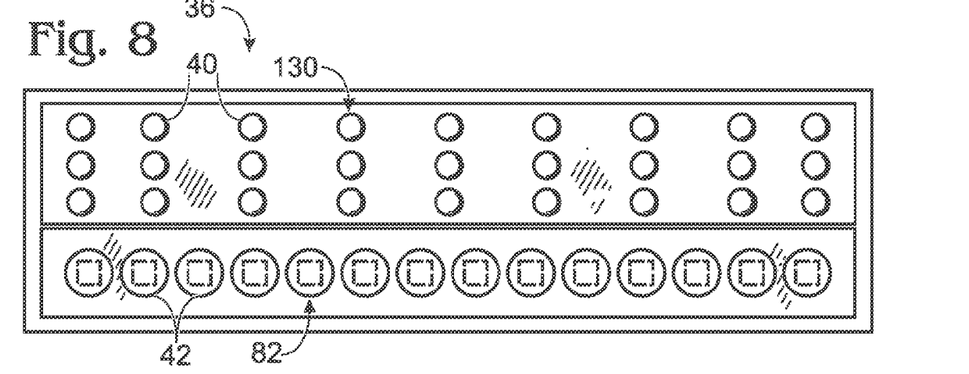
FIG. 8 is a top view of another embodiment of a light assembly for the system of FIG. 1, with the assembly including three rows of spotlights in an array, in accordance with aspects of the present disclosure.

FIG. 8 shows another exemplary light assembly 36 for system 20 of FIG. 1. The light assembly includes an array 130 having three rows of spotlights 40. The rows are uniformly spaced in the depicted embodiment, but may have nonuniform spacing in other embodiments. The columns of spotlights may or may not be uniformly spaced.

Figure 9:
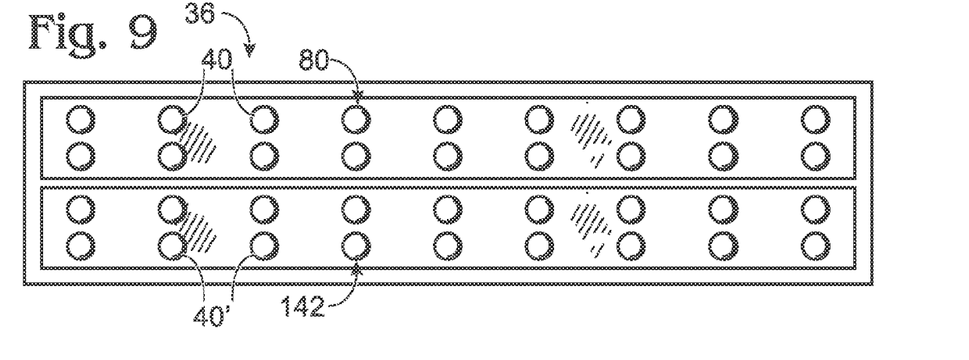
FIG. 9 is a top view of yet another embodiment of a light assembly for the system of FIG. 1, with the assembly including two arrays of spotlights for excitation with different wavelengths of light, in accordance with aspects of the present disclosure.

FIG. 9 shows yet another exemplary light assembly 36 for system 20 of FIG. 1. The light assembly includes two arrays 80, 142 of spotlights 40, 40' for excitation with different wavelengths of light.

Figure 10:
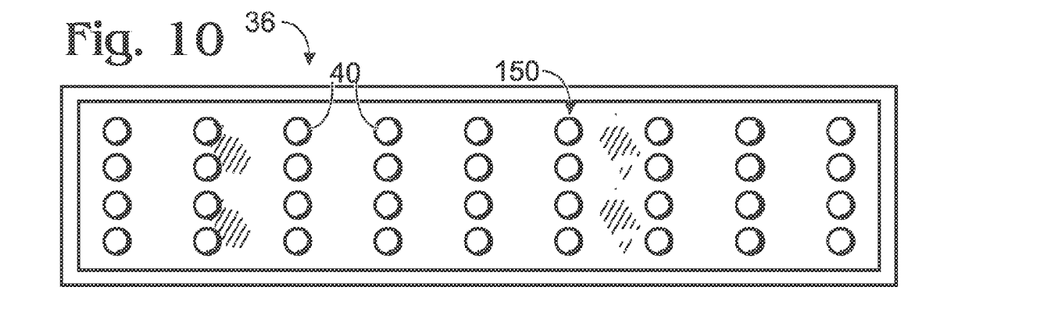
FIG. 10 is a top view of still another embodiment of a light assembly for the system of FIG. 1, with the assembly including four rows of spotlights to produce all of the excitation light of a given wavelength for the system, in accordance with aspects of the present disclosure.

FIG. 10 shows still another exemplary light assembly 36 for system 20 of FIG. 1. The assembly has a single array 150 with four rows of spotlights 40. The spotlights are evenly spaced within each row, and the rows are evenly spaced from one another. Array 150 may contain all of the spotlights for a given wavelength or may be supplemented with one or more additional arrays of spotlights 40 (e.g., see FIGS. 1 and 2).

Figure 11:
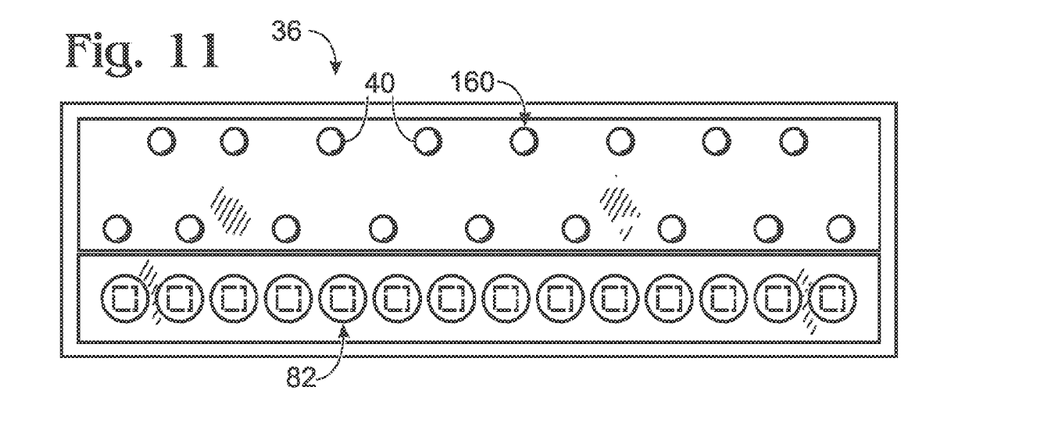
FIG. 11 is a top view of still yet another embodiment of a light assembly for the system of FIG. 1, with the assembly including a pair of staggered rows of spotlights, in accordance with aspects of the present disclosure.

FIG. 11 shows still yet another exemplary light assembly 36 for system 20 of FIG. 1. The assembly includes an array 160 composed of a pair of staggered rows of spotlights 40.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

What is claimed is:

1. A system for sample analysis, comprising:
   a microplate having wells;
   a support member to hold the microplate in an examination area;
   one or more arrays of a plurality of spotlights being closer to one another near both ends of each array relative to a central portion of such array between the ends, each spotlight producing excitation light of a same wavelength or waveband that simultaneously illuminates a plurality of the wells while the microplate is held in the examination area;
   a detector to detect light emitted from wells of the microplate in response to illumination with the excitation light; and
   a processor programmed to determine a characteristic of samples contained in wells of the microplate based on the light detected.

2. The system of claim 1, wherein the one or more arrays include a first array and a second array that are spaced from each other and arranged obliquely to each other and obliquely to the microplate.

3. The system of claim 1, wherein the plurality of spotlights in each array are arranged in two or more rows.

4. The system of claim 1, wherein the detector has a nonuniform spatial sensitivity to the emitted light received from different regions of the examination area, and wherein the spotlights are arranged to illuminate the examination area unevenly to compensate for the nonuniform spatial sensitivity of the detector.

5. The system of claim 4, wherein the spotlights are arranged to illuminate regions for which the detector has lower sensitivity with more light and regions for which the detector has higher sensitivity with less light.

6. The system of claim 1, wherein the one or more arrays illuminate the examination area with ultraviolet light of a first wavelength or waveband, further comprising one or more other arrays of lights to illuminate the examination area with visible and/or ultraviolet light of a second wavelength or waveband different from the first wavelength or waveband.

7. The system of claim 6, wherein the one or more other arrays are composed of floodlights.

8. The system of claim 1, wherein the microplate has a footprint, and wherein each spotlight has a maximum intensity and illuminates less than about one-fourth of the footprint at half maximal or greater intensity.

9. The system of claim 1, wherein each spotlight has an angular beam width of no more than about 25 degrees.

10. The system of claim 1, wherein spotlights of each array have beams that are not parallel to each other.

11. A system for sample analysis, comprising:
    a microplate having wells;
    a support to hold the microplate in an examination area;
    at least two arrays of LED spotlights, each LED spotlight producing excitation light of a same wavelength or waveband that simultaneously illuminates a plurality of the wells while the microplate is held in the examination area, each array having at least two rows each formed by a plurality of the LED spotlights having a nonuniform spacing within each row;
    a detector to detect light emitted from wells of the microplate in response to illumination with the excitation light; and
    a processor programmed to determine a characteristic of samples contained in wells of the microplate based on the light detected.

12. The system of claim 11, wherein the at least two arrays emit ultraviolet light of a first wavelength or waveband, further comprising at least two other arrays each including a plurality of light sources that emit ultraviolet light of a second wavelength or waveband different from the first wavelength or waveband.

13. The system of claim 12, wherein the at least two arrays produce excitation light of about 335-345 nm and the at least two other arrays produce excitation light of about 375-395 nm.

14. The system of claim 11, wherein the microplate contains samples that include a calcium-binding luminophore.

* * * * *